(12) United States Patent
Aner

(10) Patent No.: US 10,765,772 B2
(45) Date of Patent: Sep. 8, 2020

(54) NATURAL METHOD OF REDUCTION AND REMOVAL OF PATHOGENIC AGENTS AND MICROORGANISMS CONTAINED IN SOLIDS

(71) Applicant: Andres Adalberto Aner, Buenos Aires (AR)

(72) Inventor: Andres Adalberto Aner, Buenos Aires (AR)

(*) Notice: Subject to any disclaimer, the term of this patent is extended or adjusted under 35 U.S.C. 154(b) by 444 days.

(21) Appl. No.: 15/480,943

(22) Filed: Apr. 6, 2017

(65) Prior Publication Data

US 2018/0050125 A1 Feb. 22, 2018

(30) Foreign Application Priority Data

Aug. 16, 2016 (AR) .............................. P20160102511

(51) Int. Cl.
| | |
|---|---|
| *A61L 9/00* | (2006.01) |
| *F26B 13/10* | (2006.01) |
| *B02C 11/08* | (2006.01) |
| *A61L 11/00* | (2006.01) |
| *B02C 18/06* | (2006.01) |
| *B02C 18/22* | (2006.01) |
| *B09B 3/00* | (2006.01) |

(Continued)

(52) U.S. Cl.
CPC .............. *A61L 11/00* (2013.01); *B02C 18/06* (2013.01); *B02C 18/2233* (2013.01); *B09B 3/0083* (2013.01); *A61L 2/04* (2013.01); *B02C 18/146* (2013.01); *B02C 2201/06* (2013.01)

(58) Field of Classification Search
CPC ..... A61L 2/00; A61L 2/04; A61L 2/07; A61L 11/00; B09B 3/0083; B02C 18/2233

USPC ........ 422/1, 26–28, 32–33, 184.1, 261, 292, 422/295, 297, 300, 307–309; 34/523; 241/65, 171, 185.5, 606

See application file for complete search history.

(56) References Cited

U.S. PATENT DOCUMENTS 5,217,688 A * 6/1993 Von Lersner ............. A61L 2/24
241/23

* cited by examiner

*Primary Examiner* — Monzer R Chorbaj

(57) ABSTRACT

A method for the reduction and/or removal of pathogenic agents and microorganisms contained in solids, comprising the steps of purification of the starting material to dispose of materials that combine a great size and extreme hardness and malleability; and the adjustment of the humidity degree of the material obtained in step of purification, and the grinding and heating of the material obtained in the step of adjusting the humidity, where the grinding and heating are carried out simultaneously by subjecting the material to a high pressure while at the same time its temperature is increased by means of an increase in the pressure on the material and the friction caused between the material and the grinding means. And A machine to carry out the method, comprising a front chamber for the entrance of the material; a contiguous rear chamber associated with the entrance chamber, by means of which the processed material is expelled; said contiguous rear chamber containing a grinding means that rotates when it is actuated by an engine; and a piston that enters into the front chamber running along said chamber into the rear chamber until it reaches a grinding means, where the grinding means consists of a solid, hard and heavy cylinder associated with a transverse axis, said cylinder being provided with a set of longitudinal slots from base to base that form edges with the cylinder surface.

7 Claims, 4 Drawing Sheets

(51) Int. Cl.
*A61L 2/04* (2006.01)
*B02C 18/14* (2006.01)

NATURAL METHOD OF REDUCTION AND REMOVAL OF PATHOGENIC AGENTS AND MICROORGANISMS CONTAINED IN SOLIDS

This invention is directed to a method and a machine for the reduction and/or removal of pathogenic agents and microorganisms in solids by means of physical mechanisms. The method may be used for the treatment of urban wastes or organic wastes from factories that produce organic wastes or for the reduction and/or removal of pathogenic agents and microorganisms of food which process requires the grinding of raw material and, in general, for the grinding and reduction and/or removal of pathogenic agents and microorganisms in solids.

BACKGROUND

The treatment of solids having organic contents, the disposal of waste and, particularly, the disposal of waste masses are a current problem, with public dumping sites being rapidly filled up and contaminating leachates therefrom being a frequent contaminant of waterways. Urban and industrial wastes always contain or degrade forming toxic products or polluting gas products.

The processes frequently used for the treatment of this kind of wastes containing organic products are usually thermal, biological or chemical processes. The problems associated with said current thermal treatments include the need of making high investments and high maintenance costs mainly due to the energy cost and physical conditions that make it difficult to apply them. As far as biological and chemical treatments are concerned, there also arise problems related to the required high investments as well as a high consumption of reactants, and, consequently, associated high costs of exploitation, a high production of treatment process wastes and the existence of physical constraints that also make it difficult to apply them.

Likewise, said wastes are usually treated and disposed of by means of cementation and burial or dumping of the solid waste product. This method of disposal has the problem of disposal of the supernatant liquid of the cementation process as well as the disposal of an increased volume of solid material which may often leach.

For example, patent WO 90/12251 discloses a method and an apparatus for waste treatment that includes grinding bulk wastes from a broad variety of sources, mixing the waste material with a binder, granulating the mixture, coating the granules with a refractory material and subjecting the mixture to combustion within a furnace at a temperature above 1300 degrees Celsius (2372.00° F.).

Likewise, patent WO 9701064 A1 discloses a method of mud treatment to achieve a non-explosive mixture that may be incinerated.

It seems difficult to omit the incineration process, which, although on the one hand neutralizes toxic organic elements, the result thereof pollutes the environment.

At present, for the disposal of said wastes, besides the incineration system, the Controlled Dump system is used. The Controlled Dump is the most commonly used means and one of its main problems is its relative short life due to a rapid saturation. On the other hand, the current guidelines of the European Economic Community with regard to this kind of dumps require that the risk of wastewater pollution by leachates be eliminated and that a suitable treatment be provided to the biogas that may be produced, all of which is costly and difficult to comply with in practice. The trend in the treatment of waste having organic contents is the biological treatment for obtaining biogas. The energy contained in the vapor that is released from the remaining mud is also usually leveraged and, finally, said mud is dried and incinerated.

DESCRIPTION OF THE INVENTION

This invention is directed to a natural method of reduction and/or removal of pathogenic agents and microorganisms in solids by means of a physical-thermal mechanism.

The proposed method consists in grinding and heating—without incineration—solid materials from different sources.

The solid materials that are the subject-matter of this method:
- do not require a previous grinding, except the extraction of extremely hard materials which volume exceeds 100 $cm^3$ (6.10 $inch^3$), such as paving stones, boulder, metals, etc.
- are previously adjusted to a preferred humidity degree by means of the addition of water or aggregates (rubble, bricks, clay, ash) in order to increase or decrease their humidity, respectively.

The device used for the execution of the method comprises a material feeding trough (1) connected to a front chamber (2) by means of a gate (3); said front chamber (2) drives an hydraulic piston (4) that pushes the material towards a rear chamber (5) containing a quasi-solid cylinder (6), a gate (7) that separates both chambers according to the device version, and another gate (8) that is actuated by means of another hydraulic piston (9) that enables the discharge of the already processed material. Likewise, the machine has means to rotate the cylinder (6) and pressure and temperature control and regulation means linked to the controls of the piston (4) and the engine associated with the cylinder (6).

The solids so prepared enter through the feeding trough (1) into the front chamber (2), after which there is another rear chamber (5) that contains on its rear end a quasi-solid cylinder (6) that rotates around a longitudinal axis (10) that transversely passes through the rear chamber (5). Said cylinder (6) includes on its surface longitudinal slots (11) having sharp edges (12) of between 60 and 120 degrees, preferably between 80 and 100 degrees. These longitudinal slots (11) play the role of bump, dragging, crushing, grinding, and friction of the entered solid material. The rear chamber (5) containing the cylinder includes an exit gate (8) in its rear end in order to enable the exit of the processed material.

The front chamber (2) includes on its upper end an opening for the entrance of a piston (4) having a concave surface in correspondence with the surface of the quasi-solid cylinder (6).

The rear chamber consists of two sections, a front section in correspondence with the front chamber in order to enable the piston passage between both chambers and a rear section that contains the cylinder and which wall, in correspondence with the cylinder shape, is concave, as a drum section, thus forming a cylindrical surface, with a tiny light between said walls and the cylinder for the movement of the material under process. Said light has a distance of up to 5 mm (0.19685 inch), preferably between 1 mm (0.0393701 inch) and 5 mm (0.19685 inch) and said light is uniform along the whole concave section of said wall.

The device used to carry out the process has two versions, one of which is in upright position (FIG. 1) and the other one is in a horizontal position (FIG. 2).

In the case of the device in a horizontal position (FIG. 2), between the entrance trough (1) and the base of the front chamber (2) there is an intermediate cap or gate (3) associated with the piston that prevents wastes from entering when the piston (4) moves towards the rear chamber (5). The cylinder (6) starts rotating at high speeds and the piston (4) moves into the front chamber (2) closing the trough (1) and pushing the material towards the cylinder (6).

The cylinder (6), by means of its longitudinal slots (11), while rotating, bumps, crushes and grinds the solid material and at the same time it centrifugally expels said material towards the piston (4). The piston (4) moves forward towards the cylinder (6) until finally the resulting product as a dough increases its temperature mainly owing to the pressure increase caused by the piston, the centrifugal force of the cylinder, and the friction caused by the cylinder (6) against the dough. At a certain pressure and when a part of the dough becomes powdered, the dough moves between the cylinder surface (6) and the light that remains between the cylinder and the concave wall (13) of the rear chamber (5), being subjected to a greater friction and converted into a ground and homogeneous dough, thus making the rapid and homogeneous distribution of heat in the material easier. The water vapor produced by the process, acting at a high pressure, is not only responsible for most of the temperature increase and the homogeneous distribution of heat in the mixture but also it acts as a pressure retainer mixed with the dough.

Once the desired temperature and exposure times have been reached, the exit gate (8) opens and the inner pressure is released thus leveling both (inner and outer) pressures. The first element that exits is water vapor and the second one is the processed dough.

The joint action of the temperature and vapor causes the coagulation of the microorganism proteins, among which there are essential proteins for the microorganism life and reproduction, consequently, this fact leads to their destruction.

The grinding of the wet material until it becomes a dough eases the action of temperature and vapor, thus ensuring that said physical-chemical conditions reach all of the material.

In the upright position device version (FIG. 1), the material enters into the trough (1) and falls onto a gate (7) that separates the front chamber (2) from the rear chamber (5). When the material load is finished, the gate (3) of the trough (1) is closed, the cylinder (6) starts rotating at high speeds, the gate (7) that separates both chambers (2 and 5) opens and the piston (4) moves forward into the tunnel formed by the front chamber (2) and the rear chamber (5) thus pressing the material against the cylinder (6).

PREFERRED EMBODIMENTS

Figure 1:
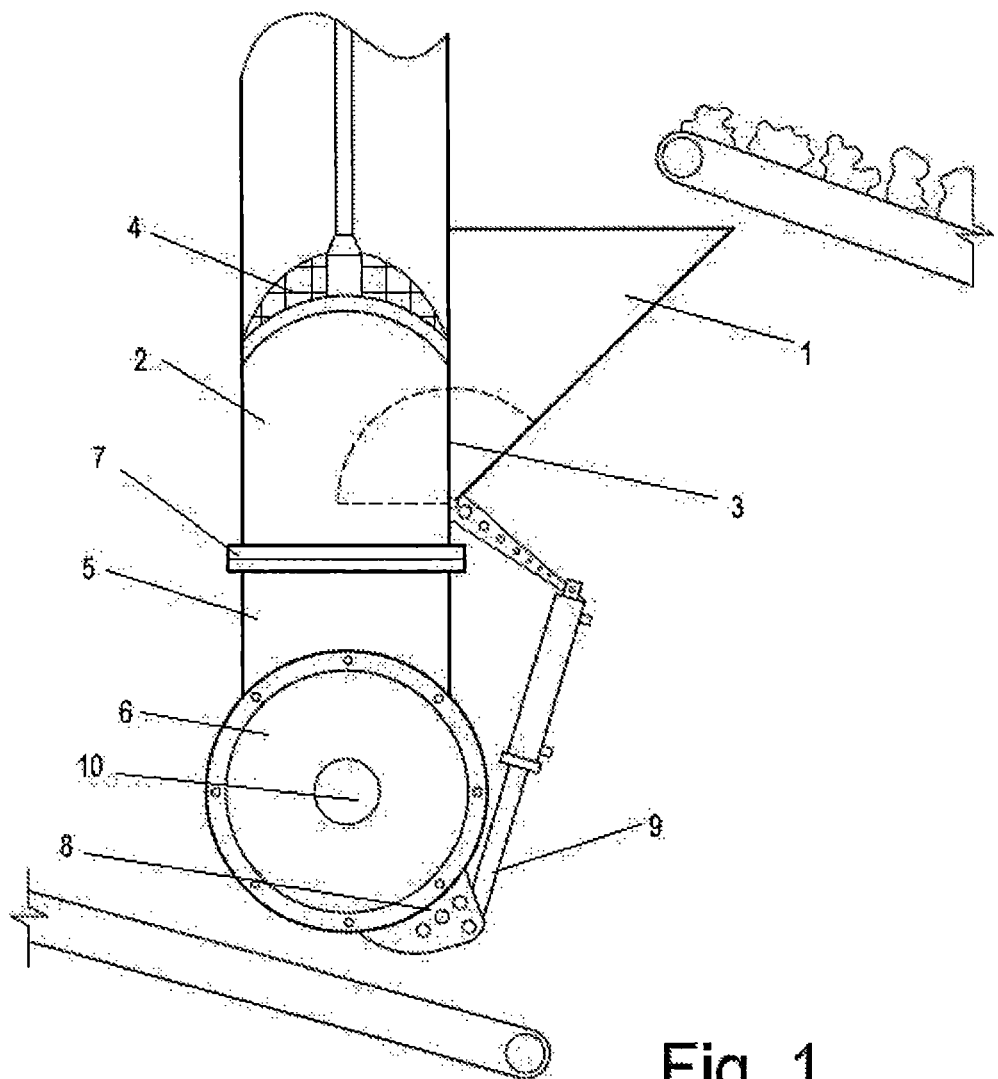
FIG. 1 represents the device in upright position.
Figure 2:
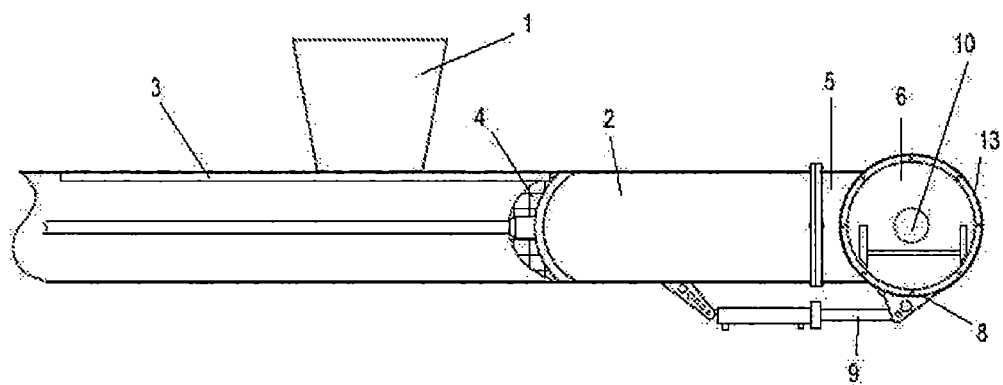
FIG. 2 represents the device in a horizontal position.

As there arises from the description of the invention, the method consists of the following steps:

Purification of the starting material

Adjustment of its humidity degree

Load of the material

Simultaneous grinding and heating of the material at high pressure

Discharge of the obtained dough a) Purification of the starting material

The starting materials of this method do not have uniform contents, sizes, or hardness and must be previously purified in order to preserve the grinding mechanism. The grinding mechanism might be damaged by the presence of materials that combine a big size and an extreme hardness and malleability. For example, metals are extracted in view of their difficulty being ground, paving stones and boulder exceeding a volume of about 100 cm$^3$ (6.1023744094732 inch$^3$) whenever they do not enable an easy grinding or compromise the integrity of the machine because of their size and hardness. For example, if the starting material is fragile, such as animal bones and fat as waste of the food industry, a starting purification shall not be necessary in view of the fragility of the bone, which shall be broken by the piston action.

b) Adjustment of the humidity degree

In order to carry out the method and achieve the simultaneous grinding and heating, humidity plays a significant role to optimize said process. In this sense, in this step, aggregates, ash, and/or rubble will be added or a previous drying process will be used in order to reduce the percentage humidity of the starting material, otherwise water should be added.

c) Material load

The material is loaded through the trough (1) into the front chamber (2).

d) Simultaneous grinding and heating of the material at high pressure

The material enters into the machine through the trough (1) towards the front chamber (2) that receives the material. The cylinder (6) starts rotating up to the process starting speed. Once the entrance of the material has been completed, the gate (3) of the trough (1) is closed and the piston (4) moves onto the material.

The material contacts the cylinder (6) that is rotating at high speed and the edges (12) of the slots (11) of the cylinder attack the material. Simultaneously, the piston (4) exerts pressure onto the material towards the cylinder (6). The cylinder (6) speed and the shape of its slots (11), by the action of the centrifugal force, prevent the material from entering into the slots (11) of the cylinder (6). Likewise, the edges (12) of the slots grind the material until it becomes powdered.

When the material becomes a dough, said dough is dragged by the cylinder (6) between the light existing between said solid and the inner cylindrical surface (13) of the rear chamber (5) thus contributing to further reduce the size of the material particles. Owing to both friction and the pressure increase, heat is created, which increases the dough temperature and, in turn, the existence of vapor at high pressure and the reduction of the material particle size 1 contribute to a more rapid and uniform heat distribution.

Once the target temperature has been obtained, it is kept during the target time in order to achieve the reduction and/or removal of the pathogenic material and microorganisms.

e) Discharge of the obtained dough

Once the process has finished, the inner and outer pressures are balanced, the discharge gate (8) is opened and the material is expelled.

Thus, for example, the process may be carried out at a target temperature from 72 to 91 degrees Celsius (from 161.6 to 195.8° F.) for 3 to 15 seconds or from 92 to 138 degrees (197.6 to 280.4° F.) for 5 to 20 seconds, or other values that are part of the state of the art with regard to the removal of pathogenic material and reduction of the amount of microorganisms.

In order to achieve a greater reduction of the pathogenic material and microorganisms in the material, it is possible to use a target temperature from 115 to 136 degrees Celsius (239 to 276.8° F.) for 21 seconds to 3 minutes or other values of a process of reduction and/or removal of pathogenic agents and microorganisms that are part of the state of the art and generally associated with pasteurization and sterilization processes.

Likewise, humidity may be added also in the humidity adjustment step by means of an acidic solution in order to vary the pH of the medium and contribute to the efficiency of the process of pathogenic material removal and reduction of the amount of microorganisms.

The operating pressure of the machine may reach 7 $kg/cm^2$, preferably a pressure from 2 to 5 $kg/cm^2$ to carry out the process and the operating speeds of the cylinder (6) are between 2400 and 4000 rpm (revolutions per minute), which will enable to reach the proposed temperatures.

Both the piston (4) pressure and the cylinder (6) speed are subject to the target temperature. Therefore, pressure and speed are determined by the target temperature of the process. The machine includes temperature sensors associated with the engine that actuates the cylinder (6) and the piston (4) in order to regulate the cylinder (6) speed and the piston (4) pressure so that the target temperature is achieved and kept during the desired time.

The quasi-solid cylinder (6) is given this name because it includes a series of slots or cuts (11) along the cylinder trunk, from base to base and from the surface and towards its inner axis, which preferred depth is of at least a tenth part of the cylinder diameter, thus forming rims or edges (12) on the cylinder trunk surface, which attack the material and grind it. Said slots (11) are spaced along the diameter in an enough amount and with an enough size so as not to weaken the cylinder structure (6) for the work it must do. In the accompanying figures, the cylinder includes six evenly distributed slots.

Figure 3:
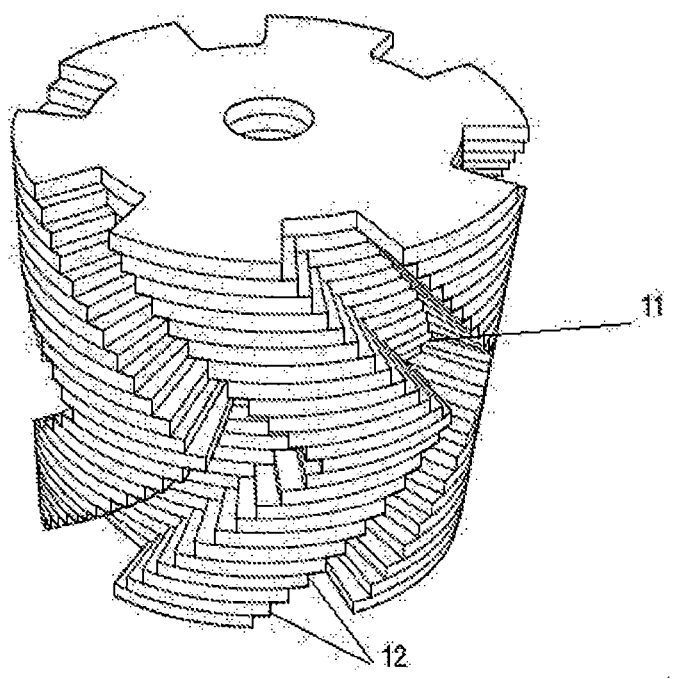
FIG. 3 is a side view of the quasi-solid cylinder with longitudinal slots with a vertex.
Figure 4:
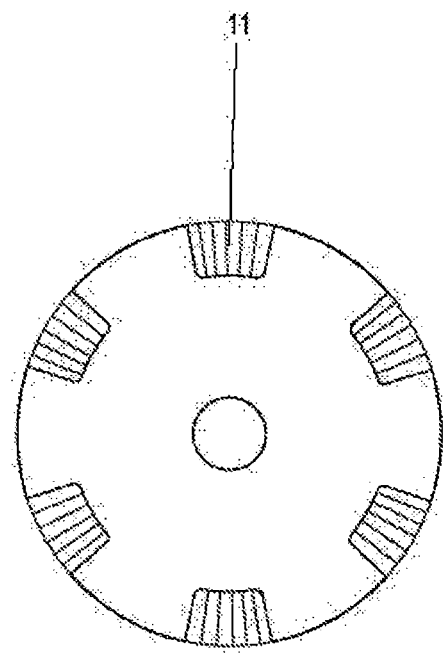
FIG. 4 is a top view of the quasi-solid cylinder with longitudinal slots with a vertex.
Figure 5:
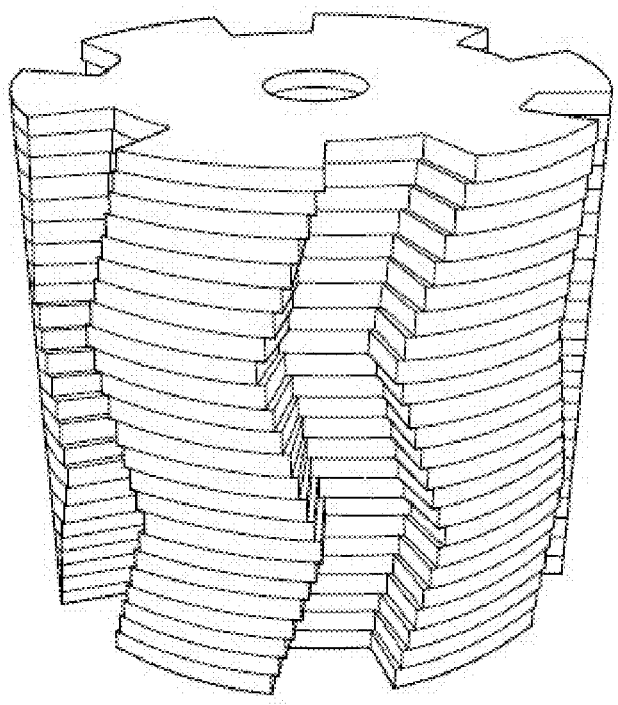
FIG. 5 is a side view of the quasi-solid cylinder with longitudinal slots with two vertexes.
Figure 6:
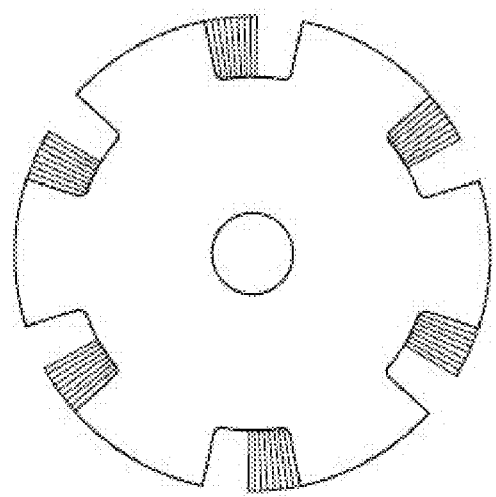
FIG. 6 is a top view of the quasi-solid cylinder with longitudinal slots with two vertexes.

Said slots are V shaped in a cylinder version (FIGS. 3 and 4) formed by a vertex. In another version of the cylinder, the slots have a bigger angle between the sides that form the vertex and have two vertexes (FIGS. 5 and 6).

The slots and edges thereby formed may also be teethed, as shown in the accompanying figures. Said feature contributes to the grinding efficacy since it creates a significant amount of vertexes on the edge thus increasing the grinding capability. Said feature also results from the practicality and economy that derive from the cylinder assembly as a series of cylindrical plates with a shape corresponding to the cylinder base that stack up and successively move to form the slots and then said cylindrical plates join together to form the cylinder (6).

Furthermore, the angle formed by the slots with regard to the trunk surface is relevant. Said angle, as may be seen in the top view of the cylinders is slightly above 90 degrees. Said aspect is convenient so that a centrifugal force is created with regard to the area within the slot when the cylinder rotates. At the same time, it is not convenient that said angle be much greater than 90% in view of the fact that the efficacy in the action of the edges would be lost when the material is ground.

The cylinder must be build with material of a hardness and weight that enables the grinding of any kind of material, in a rapid and effective way, without compromising the integrity of the machine. In this sense, the cylinder will be perfectly balanced on a hard, rigid and perfectly straight axis, which will enable the stable and safe rotation at great speeds.

The so formed quasi-solid cylinder with the drum containing it and the small light between them is responsible for the thorough grinding of the material and, consequently, it has been formed with slots in a solid body since if it were formed with protruding parts and without the safeguard of a solid body to bear the stress, it would cause a rapid wear of the protruding parts as well as an eventual breakdown and detachment of said protruding part with the risk it represents for the integrity of the machine and its operators.

Embodiment Example

For a concrete case of material treatment, 10 kgs of solid material are added, said solid material being composed of organic and inorganic waste with 23% humidity content. The piston (4) moves towards the cylinder but without exerting pressure onto the dough. The material collides with the cylinder that is rotating at a speed of 2400 rpm, thus starting breaking and grinding the material. Next, the piston moves onto the material increasing the pressure up to 5 kg/cm2 and at the same time the cylinder increases its rotation speed to reach a speed of 3800 rpm. In this way, the material is powdered and there is a significant pressure increase that alters the composition of said dough as well as a temperature increase until the target temperature is reached which turns out to be uniform in all of the particles of said dough. Once the temperature is reached, the process ends with the opening of the discharge gate from which unpolluted water vapor and the material processed as an inert, unpolluted dough, free of pathogenic agents and microorganisms exit.

The invention claimed is:

1. A method for the reduction and/or removal of pathogenic agents and microorganisms contained in solids, comprising the following steps:
   a) providing a front chamber for the entrance of the starting material; a contiguous rear chamber associated with the entrance chamber, by means of which the processed material is expelled; said contiguous rear chamber containing a grinding means that rotates when it is actuated by an engine; and a piston that enters into the front chamber running along said chamber into the rear chamber until it reaches a grinding means, where the grinding means consists of a solid, hard and heavy cylinder associated with a transverse axis, said cylinder being provided with a set of longitudinal slots from base to base that form edges with the cylinder surface, where the light existing between the solid cylinder and the drum containing it is smaller than 5 mm, b) Purification of the starting material to dispose of materials that combine a size over 10 cm3 and hardness similar to boulder or paving stone and malleability as metal, c) Adjustment of the humidity degree of the material obtained in step b), d) Grinding and heating and pressurizing simultaneously the material obtained in step c), where the grinding and heating and pressurizing of step d) are carried out simultaneously by grinding the material until the material is powdered; and by means of friction of the powdered material between the light existing between the solid cylinder rotating and the drum containing it, plus the pressure of the piston advancing towards the grinding cylinder, heating and pressurizing is obtained, thus converting water into steam until the desired temperature is reached.

2. The method of claim 1, comprising that the simultaneous grinding and heating process is carried out in an operating pressure range between 3 kg/cm2 and 7 kg/cm2.

3. The method of claim 2, comprising that the material heating target temperature is in the range from 72° C. to 138° C.

4. The method of claim 3, comprising that the time during which the material is subjected to the target temperature is in the range from 1 second to 3 minutes.

5. The method of claim 4, comprising that the time during which the material is subjected to a temperature in the range from 72° C. to 91° C. is within a range between 3 and 15 seconds.

6. The method of claim 4, comprising that the time during which the material is subjected to a temperature in the range from 92° C. to 138° C. is within a range between 5 and 20 seconds.

7. The method of claim 4, comprising that the time during which the material is subjected to a temperature in the range from 115° C. to 136° C. is within a range between 21 seconds and 3 minutes.

* * * * *